United States Patent [19]

Salyer

[11] Patent Number: 5,501,686

[45] Date of Patent: Mar. 26, 1996

[54] TOOL DRIVER

[75] Inventor: Brian D. Salyer, Warsaw, Ind.

[73] Assignee: Othy, Inc., Warsaw, Ind.

[21] Appl. No.: 83,094

[22] Filed: Jun. 25, 1993

Related U.S. Application Data

[60] Division of Ser. No. 858,935, Mar. 27, 1992, Pat. No. 5,282,804, which is a continuation-in-part of Ser. No. 696,951, May 8, 1991, Pat. No. 5,171,313.

[51] Int. Cl.$^6$ .................................................. A61B 17/00
[52] U.S. Cl. .................................................. 606/79; 606/83
[58] Field of Search .................................. 606/79, 80, 81, 606/82, 83, 85–88, 180; 407/61, 62, 63, 54, 58, 59; 408/206, 207, 703

[56] References Cited

U.S. PATENT DOCUMENTS

| | | | |
|---|---|---|---|
| 2,437,014 | 3/1948 | Arnesen | 606/100 |
| 4,341,206 | 7/1982 | Perrett | 606/96 |
| 4,987,904 | 1/1991 | Wilson | 606/86 |
| 5,089,004 | 2/1992 | Averill | 606/85 |
| 5,171,313 | 12/1992 | Salyer | 606/86 |
| 5,180,384 | 1/1993 | Mikhail | 606/79 |
| 5,190,548 | 3/1993 | Davis | 606/79 |

Primary Examiner—Michael A. Brown
Attorney, Agent, or Firm—Lundy and Associates

[57] ABSTRACT

A tool driver having a shaft with a longitudinal axis and opposite ends. A boss is positioned at one of the ends. A tool collet is positioned at the other of the ends. The boss has a bore extending axially thereof forming debris cavity. An actuator on the shaft. A pair of oppositely disposed pins on the actuator. The pins are movable in relation to the boss in response to movement of the actuator. The actuator and the pins move as a unit axially of the boss between an at rest position and a static position. The pins are movable between an extended position and a retracted position as the actuator moves between an at rest position and a static position, whereby a tool can be positioned on the tool driver when the actuator is in its static position and held in operable position on the tool driver when the actuator is in its at rest position.

21 Claims, 4 Drawing Sheets

TOOL DRIVER

This application is a division of 07/858,935, filed 03/27/92, now U.S. Pat. No. 5,282,804, which is a continuation in part of Ser. No. 07/696,951, filed 05/08/91, now U.S. Pat. No. 5,171,313.

BACKGROUND OF THE INVENTION

The present invention pertains to holders for rotary tools, and more particularly pertains to a tool driver suitable for use with acetabular reamer cups, patella cutters or other surgical tools which are secured onto a tool driver by diametrically opposed pins.

Acetabular reamer cups are surgical tools which are used to cut hemispherical cavities in pelvis bones for the insertion of artificial hip joints. Patella cutters are surgical tools, which are used to cut or shape the under side of the patella or knee cap during knee replacement surgery. A patella cutting system is generally composed of a cutter mounted on a tool driver, which in turn is mounted in the chuck or collet of a portable drill or flexible powered shaft. Cutters for patella cutting systems have a complex arrangement of precisely shaped cutting edges extending outwardly from a flat planer surface.

Unique to knee surgery and some hip operations is the utilization of milled bone, tissue and debris as filler to be placed between the artificial inset and the body to assist the healing process. Acetabular reamer cups and patella cutters are mounted on tool drivers, which in turn are mounted in the chuck or collet of a portable drill or flexible powered shaft. Both tools are separable from their tool drivers to replace or sharpen as they are used. It may be necessary to change tools during an operation, for example. Tool drivers are not inexpensive and must be cleaned and reused.

Some previous tool drivers grip the tool without the use of opposed pins by means of a flange and slot and an opposed spring-loaded ball catch, like that on a socket wrench or socket driver or other catch devices. This represents a problem in that the catch tends to trap dried blood and other debris, which is very difficult to remove during cleaning. An additional problem is that unless tolerances of tools and tool drivers are made very close, at greatly increased cost, there is considerable free play between the tool and tool driver. This increases wear and decreases the precision of the tool.

An alternative tool driver usable with acetabular reamer cups, described in Salyer, U.S. Pat. No. 4,811,632, issued on Mar. 14, 1989, has a cam and follower mechanism which provides for axial and rotary movement of a clamp. That driver avoids many of the problems presented by the ball catch, but requires a separate locking mechanism and two handed use.

The current pin type tool drivers also cannot be disassembled easily for thorough cleaning. Additionally, they have exposed trigger mechanisms which can catch and tear a surgeon's glove and are generally cumbersome to operate.

It is therefore highly desirable to provide an improved tool driver.

It is also highly desirable to provide an improved pin type tool driver which can be easily actuated to grip and release tools, such as an acetabular reamer cup.

It is also highly desirable to provide an improved pin type tool driver which can be completely disassembled for cleaning.

It is also highly desirable to provide an improved pin type tool driver which does not tend to catch bone debris.

It is also highly desirable to provide an improved pin type tool driver which can be easily joined or disjoined from an acetabular reamer cup with a single hand.

It is also highly desirable to provide an improved pin type tool driver which eliminates exposed parts which can catch and tear a surgeon's gloves, and is easily operable.

It is finally highly desirable to provide an improved pin type tool driver which meets all of the above desired features.

SUMMARY OF THE INVENTION

It is an object of the invention to provide an improved tool driver.

It is also an object of the invention to provide an improved pin type tool driver which can be easily actuated to grip and release tools, such as an acetabular reamer cup.

It is also an object of the invention to provide an improved pin type tool driver which can be completely disassembled for cleaning.

It is also an object of the invention to provide an improved pin type tool driver which does not tend to catch bone debris.

It is also an object of the invention to provide an improved pin type tool driver which can be easily joined or disjoined from an acetabular reamer cup with a single hand.

It is also an object of the invention to provide an improved pin type tool driver which eliminates exposed parts which can catch and tear a surgeon's gloves, and is easily operable.

It is finally an object of the invention to provide an improved pin type tool driver which meets all of the above desired features.

In the broader aspect of the invention there is provided a tool driver having a shaft with a longitudinal axis and opposite ends. A boss is positioned at one of the ends. A tool collet is positioned at the other of the ends. The boss has a bore extending axially thereof forming debris cavity. An actuator on the shaft. A pair of oppositely disposed pins on the actuator. The pins are movable in relation to the boss in response to movement of the actuator. The actuator and the pins move as a unit axially of the boss between an at rest position and a static position. The pins are movable between an extended position and a retracted position as the actuator moves between an at rest position and a static position, whereby a tool can be positioned on the tool driver when the actuator is in its static position and held in operable position on the tool driver when the actuator is in its at rest position.

BRIEF DESCRIPTION OF THE DRAWINGS

The above-mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
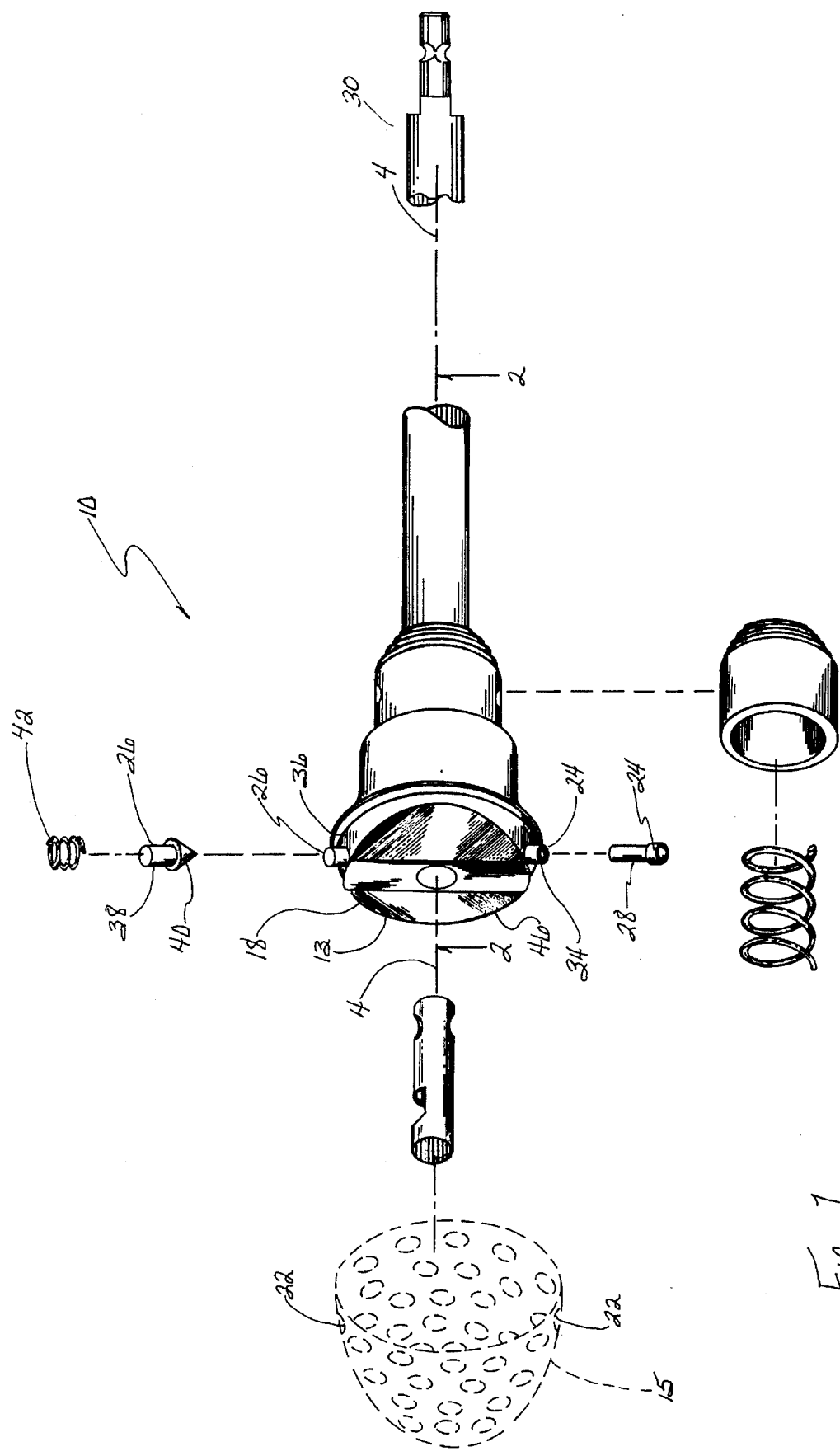
FIG. 1 is a perspective, exploded view of the tool driver of the invention.
Figure 2:
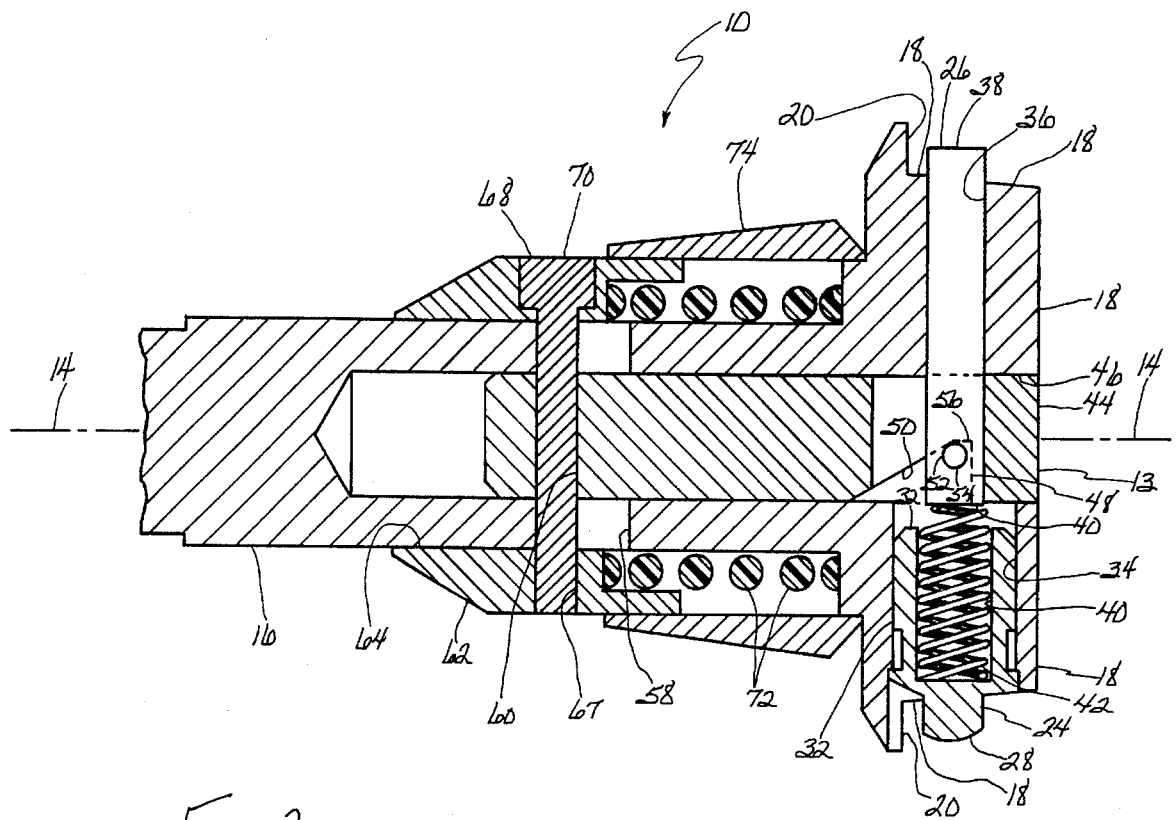
FIG. 2 is a cross-sectional view of a similar tool driver of the invention as if taken substantially along line 2—2 of FIG. 1. The action pin is in its extended position and the actuator is in its retracted position.
Figure 3:
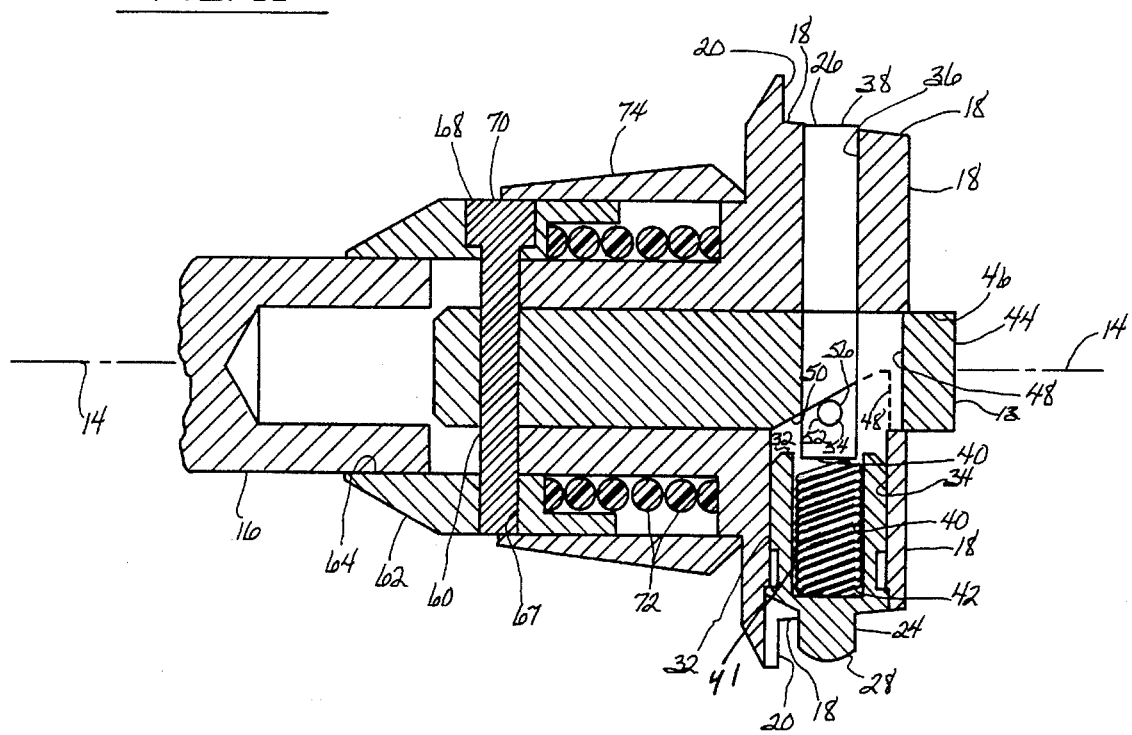
FIG. 3 is a view similar to that shown in FIG. 2 showing the action pin in its retracted position and the actuator in its extended position.

The tool driver 10 of the invention grips the base 12 of an acetabular reamer cup or other tool 15 at front end 13 and is clasped by a chuck or other holder of a portable drill or rotary shaft (not shown) at the rear end 30. Tool driver 10 has a longitudinal axis 14 and an elongated body or shaft 16. Body 16 as shown in FIGS. 1–3 has a boss 18 at end 13 surrounded by a flange 20 which extends generally perpendicularly of axis 14 outwardly of boss 18. Boss 18 is generally frusto-conical in shape, tapering from end 13 outwardly toward end 30. Flange 20 extends from the base of boss 18 radially outwardly of body 16.

Boss 18 is shaped and sized to receive thereon a tool 12 which has an open base 12. Base 12 fits over boss 18 with its peripheral edge against flange 20. Tool 15 is provided with diametrically opposite openings 22 therein through which pins 24 of tool driver 10 are positioned to secure tool 15 onto tool driver 10 with boss 18 within the tool.

Pins 24 and 26 extend in diametrically opposite directions from boss 18 radially outwardly of tool driver 10. As shown in FIGS. 2 and 3, pin 24 is provided with a distal end 28 and a threaded end 32. Threaded end 32 is positioned within a threaded opening 34 within boss 18. Latch pin 26 is positioned within a bore 36 in boss 18. Bore 34 and bore 36 are coaxial on opposite sides of axis 14. Latch pin 26 has a distal end 38 and an abutment end 40. Pin 24 has an interior bore 41 therein in which a spring 42 is positioned. Spring 42 extends from within pin 24 to engage abutment end 40 of latch pin 26.

Latch pin 26, thus, can move within bore 34 between its retracted position as shown in FIG. 3, and its extended position as shown in FIG. 2 against spring 40. Providing limits for movement of latch pin 26 is the action pin 44.

Action pin 44 is positioned within an axially extending bore 46 which extends from end 13 into shaft body 16. Action pin 44 is positioned within bore 46 and has a transversely extending bore 48 extending therethrough in which latch pin 26 is positioned. Bore 48 has an axial length of twice the diameter of latch pin 26 and a dimension transverse thereto of at least the diameter of latch pin 26. Thus, action pin 44 can move axially of both boss 18 and shaft body 16 a distance equal to at least two diameters of latch pin 26 without engaging latch pin 26.

Action pin 44 further has a stop surface 48 and a cam surface 50 thereon adjacent end 40. Stop surface 48 extends longitudinally of latch pin 26 inwardly from end 40. In the specific embodiment shown, stop surface 48 is planar and extends from side to side of action pin 44 and half way through action pin 44. Cam surface 50 also is planar and extends side to side of action pin 44, but is angularly disposed both to the axis of action pin 44 and stop surface 48. Cam surface 50 slopes outwardly of pin 44 away from end 13.

Latch pin 26 is provided with a bore 52 and a pin 54 which extends through the bore 52 radially outwardly of latch pin 26 on both sides thereof. Pin 54 has cylindrical cam surfaces 56 thereon exterior of latch pin 26. Cam surface 56 engages cam surface 50 of action pin 44 during the movement of action pin 44 axially of boss 18 and shaft body 16. This movement of the cam surfaces 50, 56 of pin 44 and 54 between opposite engagements of latch pin 26 and action pin 44 moves latch pin 26 between its retracted position and its extended position and expands and compresses spring 42.

A bore 58 of similar size to bore 48 is provided through shaft body 16 at a position spaced from end 13. Similarly, a bore 60 of a diameter generally half or less than half of the axial dimension of bore 58 is positioned remotely from bore 48 and extends through action pin 44.

A thumb trigger, or collar 62 is provided to slide on shaft body 16. Thumb trigger 62 has a bore 64 therein in which shaft body 16 is positioned. Thumb trigger 62 also has a bore 66 extending therethrough which is generally of the same size as bore 60, but with one end 67 having threads and the other end 68 being counter-bored to receive the head of a pin 70. Pin 70 extends through thumb trigger 62 through bore 60 of action pin 44 and is held in place by threaded end 66 and complementary threads on pin 70. Thus, pin 70 connects together actuator action pin 44 and thumb trigger 62. Thumb trigger 62 and action pin 44 and pin 70 thus can move relative to shaft body 16 over the limits of bores 48 and 58. In a particular embodiment, the limits to the movement of action pin 44 and thumb trigger 62 are the axial limits of bore 48. In another particular embodiment, the limits of movement of action pin 44 and thumb trigger 62 are the axial limits of bore 58.

A helical spring 72 is positioned between boss 18 of body 16 and thumb trigger 62 to urge thumb trigger 62 into its rearward or retracted position as shown in FIG. 2.

Thumb trigger 62 and action pin 44 can be moved toward end 13 against the compression of spring 72. Overlaying spring 72 and thumb trigger 62 and extending between thumb trigger 62 and boss 18 of body 16 is a sleeve 74 which remains stationary with respect to shaft body 16. Sleeve 74, both cosmetically and functionally, covers spring 72 such that spring 72 is not exposed to the exterior of tool driver 10 and is shielded from debris.

Alternate embodiments of the tool driver of the invention are illustrated in FIG. 3. In FIG. 1, latch pin 26 has camming surfaces at end 40 and action pin 44 has its camming surface 50 and its stop 48 oppositely facing that shown in FIGS. 2 and 3. In the embodiment of FIG. 1, end 40 itself rides upon camming surface 50, to move latch pin 26 from its retracted position to its extended position.

Figure 4:
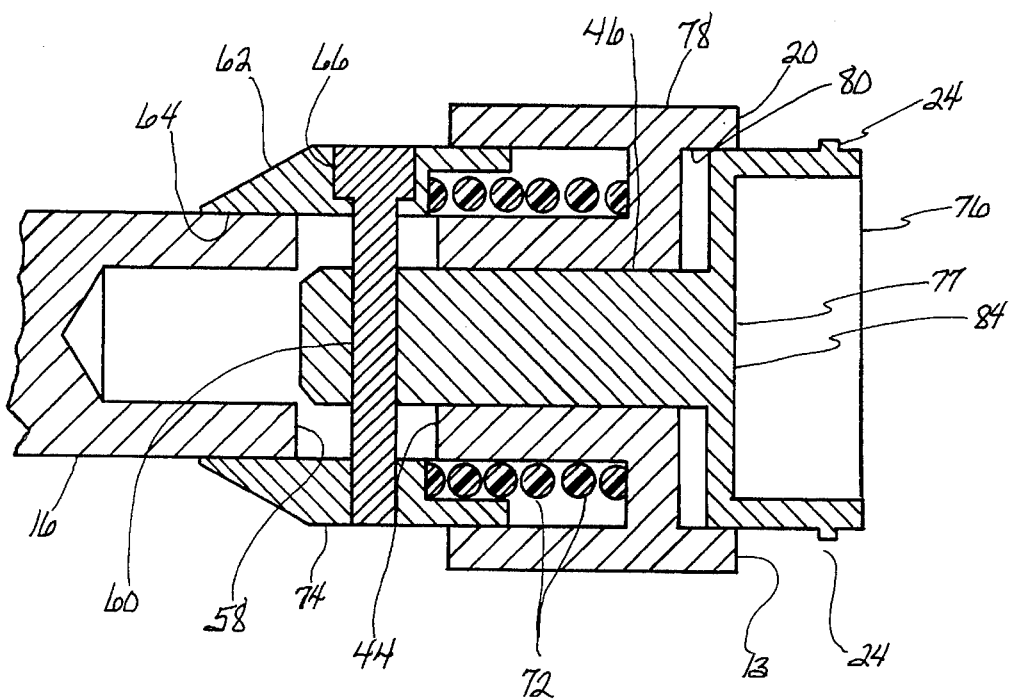
FIG. 4 is a view similar to that of FIGS. 2 and 3 showing yet another tool driver of the invention in which the boss is replaced with a cavity in which a plunger on the actuator pin is positioned.

In another embodiment shown in FIG. 4, tool driver 10 of the invention is provided with a plunger 76 secured to the end 77 of action pin 44 adjacent end 13. Shaft body 16 is provided with a boss 78 in which a cavity 80 is positioned at end 13. Cavity 80, in a particular embodiment, is a cylindrical bore coaxial of boss 78 and of shaft 16. In that same particular embodiment, plunger 76 is also cylindrical and complementary to cavity 80 such that it fits into cavity 80 when thumb trigger 62 is in its most rearward position in sliding relationship. Plunger 76 is provided with radially extending diametrically opposed pins 24. These pins are stationary pins like pin 24 above described.

Figure 5A:
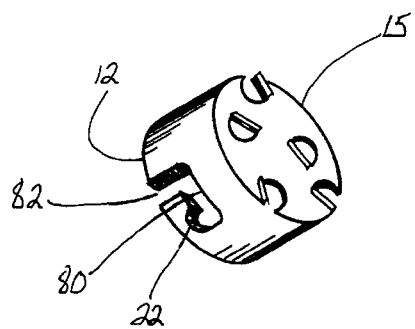
FIGS. 5, A, B, and C illustrate in perspective tools for use with the tool driver shown in FIG. 4.
Figure 5B:
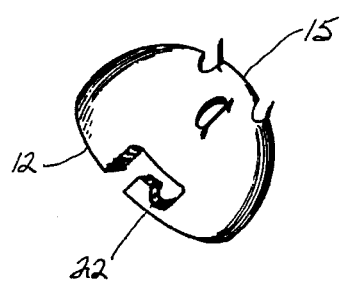
Figure 5C:
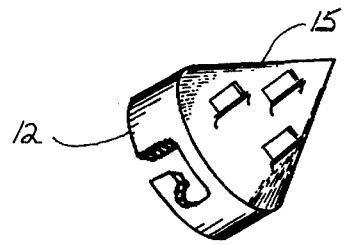

The tools for use with the tool driver 10 having the plunger 76 are like the tools above described, each provided with oppositely disposed, diametrical pin openings 22. However, each is also provided with diametrically opposite channels 80 having entrance openings 82 in which pins 24 can be positioned and caused to move so as to position pins 24 in pin openings 22. These tools, shown in three of the various configurations in FIG. 5 are available in a wide variety of tool configuartions.

In a preferred embodiment, plunger 76 is provided with a debris cup 84 therein. In some applications, it is desirable to collect bone debris for placement between a new implant and the milled portion of the bone to assist healing. In such applications, a plunger with a debris cup 84 is utilized such that debris may be collected for this use.

In operation, the tool driver 10 of the invention can be utilized to tightly grip and easily release a tool such as an acetabular reamer cup which has an open end 12 shaped complementary to boss 18 or plunger 76 and which has diametrically opposite openings for the reception of pins 24 and 26 single handedly. In order to position such a tool on the tool driver 10, the tool is positioned on boss 18 or plunger 76, and thumb trigger 62 is moved against the urging of spring 72 toward end 13.

The movement of thumb trigger 62 as shown in FIGS. 1-3 forwardly towards end 13 moves action pin 44 axially of the shaft body 16 so as to extend from boss 18, and moves pin 54 on cam surface 50, thereby retracting latch pin 26. With the thumb trigger held in its most forward position, with latch pin 26 fully retracted, one of the pin holes in the tool is positioned around stationary pin 28 and the diametrically opposite portion of the tool is positioned against flange surface 20. Thumb trigger 62 is then released upon which spring 72 urges thumb trigger 62 and action pin 44 into its most rearward position as defined by the axial limits of either bore 58 as above mentioned. When thumb trigger 62 is in its most rearward position, latch pin 26 is extended from boss 18 and both pins 26 and 28 are positioned in the diametrically opposite pin holes of tool 12. Disassembly of tool 12 from the tool driver 10 can be accomplished by the reverse of these actions.

The tool driver 10, as shown in FIG. 4, similarly functions. By urging the thumb trigger 62 toward end 13, plunger 76 is moved out of its at rest position within cavity 80. By this movement, pins 24 are moved away from end 13 of boss 78. In this position, a tool can be placed over the plunger 76, and pins 24 can be placed within the channel entrances 82 and the tool rotated so as to move the pins through channel 80 and into pin openings 22. Thumb trigger 62 is then released and spring 72 urges thumb trigger 62 into its rearward position and plunger 76 is retracted into cavity 80 thereby urging pins 24 toward boss 78 thereby resiliently securing the tool against end 13.

Figure 6:
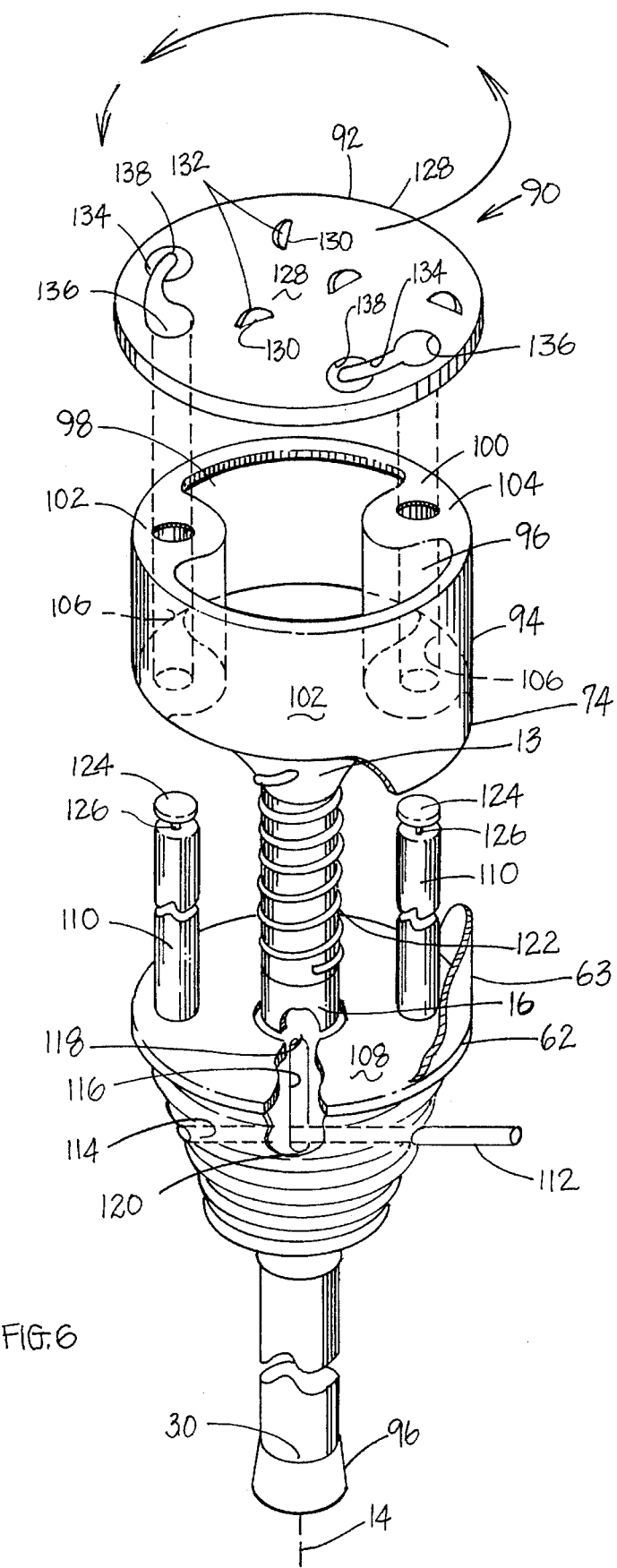
FIG. 6 is an exploded, brokenaway, perspective view of yet antoher tool driver of the invention.

Referring to FIG. 6, a tool driver 90 of the invention is shown for use with a patella cutting lid 92. The tool driver 90 comprises shaft 16 having opposite ends 13 and 30. Secured to shaft end 13 is a boss 94. Secured to shaft end 30 is a tool collet 96. Boss 94 is shown to be generally cylindrical in shape mounted coaxially on shaft 16. Boss 94 bas a debris cavity 96 therein. Debris cavity 96 extends from distal end 100 coaxially of boss 94 and of shaft 16. Debris cavity 96 has a cavity opening 98 in distal end 100 of boss 94. Debris cavity 96 extends into boss 94 from end 100 axially thereof. Sleeve 74 depends from boss 94. In the specific embodiment illustrated, debris cavity 96 is cylindrical in shape but for the provisions of oppositely disposed channel portions 102 and 104.

Channel portions 102 and 104 extend into debris cavity 96 and are provided with channels 106 which extend through channel portions 102 and 104 from shaft end 13 to boss distal end 100. Debris cavity 96 has a bottom 102 adjacent shaft end 13.

Mounted on shaft 16 is a thumb trigger 62. Thumb trigger 62 is as above described except in this embodiment is provide with cylindrical boss 63 which extends coaxially of shaft 16 tward end 13 and is in sliding relation with sleeve 74. Thumb trigger 62 has a end surface 108 facing shaft end 13 from which a pair of oppositely disposed pins 110 extend generally parallel to axis 14. Pins 110 are positioned in channels 106. Pins 110 are slideable within channels 106 and thumb trigger 62 is slideable on shaft 16. Thumb trigger 62 is connected to shaft 16 by means of a pin 112 positioned in a pin bore 114 extending transaxially of thumb trigger 62. Pin 112 is also positioned in elongated shaft slot 116. Elongated shaft slot 116 has opposite ends 118 and 120. Slot ends 118 and 120 function as stops limiting the movement of thumb trigger 62 in relation to shaft 16 and correspond to an extended position of pins 110 and a retracted position of pins 110 as will be described hereinafter. A spring 122 is positioned on shaft 16 between boss 94 and thumb trigger 62.

Both pins 110 have at their distal ends enlarged pinheads 124 separated from pins 110 by a throat portion 126. Pinheads 124 have a transaxial size similar to that of pin 110 such that pinheads may pass through channels 106. Throats 126 have a transaxial size substantially smaller than both pinhead 124 and pin 110. Throats 126 have an axial length larger than the thickness of patella cutters 92, and a transaxial size substantially smaller than both pinhead 124 and pin 110. The axial thickness of pinhead 124 is substantially less than the thickness of patella cutter 92. The reasons for these divisional limitations will become clear from the description hereinafter.

Patella cutter 92 is shown in FIG. 6 to be a disk 128 of surgical steel. Cutter 92, in a specific embodiment, is made of surgical stainless steel and formed as disclosed in U.S. Pat. No. 4,811,632, entitled "Method Of Producing An Acetabular Reamer Cup", the specification of which is incorporated herein by reference. Extending radially of patella cutter 92 are a plurality of cutting edges 130 and adjoining debris passages 132 immediately forwardly thereof in the intended direction of rotation. Debris passages 132 extend through patella cutter 92. Cutting edges 130 are spirally or radially arranged on patella cutting lid 92 and are substantially parallel to the opposite planar surfaces of patella cutter 92. Cutting edges 130 are disposed to cut upon rotation of said patella cutter 92. Cutting edges 130, upon rotation of said cutter 92 about axis 14 each sweep an area overlapped by the other of the cutting edges 130 a total of about one and one-half times. In a specific embodiment, there are two cutting edges 130 in diametrically opposite positions which cover the same territory.

In a specific embodiment, cutting edges 130 extend from the cutting lid 92 angularly to the axis 14 a height from about 0.03 to about 0.04 inches and have a length from about 0.25 to about 0.375 inches. In that same specific embodiment pin heads 124 have a thickness of less than 0.03 inches. Cutting edges 130 are always parallel to the distal planar surface of disk 128. In another specific embodiment, cutting edges 130 are radial of cutting lid 92 on radii from about 35° to about 55° apart from each other.

Patella cutter 92 also has a pair of opposed openings 134. Opposed openings 134 are elongated having an enlarged end 136 and a small end 138. Enlarged end 136 is sufficiently large to pass heads 124 of pins 110 therethrough. Small end 138 is sufficiently large to pass throat portion 126 of pins 110 therethrough, but are appreciably smaller than heads 124. Large and small ends 136, 138 of openings 134 are aligned such that each of the cutting edges 130 face small end 138. Furthermore, openings 134 are radiused so as to position the center of opening ends 136,138 spaced the same distance from axis 14 as are channels 106 such that when patella cutter lid 92 is centered on boss 94, rods 110 will be aligned with openings 134.

In a specific embodiment small ends 138 are enlarged by counter boring small ends 138 to provide a counterbore of the size of end 138 of depth of about the thickness of pin heads 124 so as to position heads 124 flush with the exterior surface of patella cutter 92 whenever throat portions 126 are positioned in small end 138.

In operation, patella cutter 92 can be easily mounted on the distal surface 100 of boss 94 by actuating the thumb trigger 62.

Thumb trigger 62 is movable axially of shaft 16 between opposite end stops 118,120 of slot 116. Spring 122 biases thumb trigger 62 and rods 110 into a retracted position in which heads 124 of rods 110 are positioned either on distal surface 100 or at a position spaced from distal surface 100 of boss 94 less than the thickness of patella cutter 92. Thumb trigger 62 is movable against the urging of spring 122 axially toward distal surface 100 of boss 94 until pin 112 is positioned against end stop 118 of slot 116. In this position, heads 124 are spaced from distal surface 100 of boss 94 a distance greater than the thickness of patella cutting lid 92 and exposing throats 126 above distal surface 100.

With thumb trigger 62 in the position in which pin 112 is against stop end 118 of slot 116 with heads 24 spaced from distal end 100 and throats 126 exposed, patella cutter lid 92 can be positioned on pins 110 by passing heads 124 through enlarged portions 136 of openings 134. Patella cutting lid 92 can then be rotated so as to position throats 126 in portions 138 of openings 134. By releasing thumb trigger 62, spring 122 urges thumb trigger 62 into its retracted position with pin 112 adjacent end stop 120 of slot 116 and heads 124 bearing upon patella cutting lid 92 within small ends thereby holding patella cutter lid 92 firmly against distal surface 100 and between boss 94 and heads 124.

In this position, patella cutting lid 92 is usable with the tool driver 90 of the invention to shave portions of the patella during surgery. The portions shaved from the patella by the cutting edges 130 pass through the debris openings 132 into the debris cavity 98 for subsequent use in the surgery, as desired, accordance with known surgical procedures. Because of the relative positioning of cutting edges 130 and the openings 134, the cutting resistance of the cutting edges 130 of the patella cutting lid 92 urge throat portions 126 against end portion 138 of openings 134 thereby securing patella cutting lid 92 to the tool holder 90 of the invention during use. In the specific embodiment in which small ends 138 are counterbored, heads 124 are fixed in ends 138 by the counterbore.

Whenever sufficient patella debris collected within the cavity 98 of boss 94 and the debris is desirably removed therefrom or patella cutter lid 92 desirably removed, thumb trigger 62 is again moved against the urging of spring 122 to position pin 112 against stop end 118. In this position of thumb trigger 62, patella cutting lid 92 can be rotated so as to position heads 124 coaxially of enlarged portions 136 of openings 134 and the patella cutting lid 92 can be removed and the patella cutting debris within the cavity 98 of the boss 94 can be removed and used as desired.

It will be noted that all of the moving parts which are exposed to the exterior of tool driver are shielded for the most part by sliding tolerances from debris. All of the intricate parts, such as the springs and the like, are enclosed within the tool driver and are not exposed to debris. Further, those surfaces which are most likely to collect debris are either smooth surfaces or surfaces like bore 34, bore 46, the exterior surface of shaft body 16 adjacent the thumb trigger, the exterior surface of thumb trigger itself, each of which may collect debris, but which are, in essence, self-cleaning by the movement of the pins and thumb triggers as above described.

Cleaning of most of the surfaces likely to collect debris can be accomplished easily without disassembly by washing the exterior of tool driver and moving thumb triggers between its most forward and most rearward positions. If more thorough cleaning is required, the tool driver can be completely disassembled, piece by piece.

By the invention, an improved pin type tool driver of the invention is provided. The improved tool driver of the invention tightly grips and easily releases pin type tools single handedly. The tool driver of the invention is provided with moving parts which do not tend to collect bone debris. Additionally, the tool driver of the invention can be cleaned without disassembly, and can be easily disassembled for thorough cleaning if desired.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A patella cutter comprising a shaft with an axis of rotation having a tool end and a collet end, a boss secured to said tool end, said boss having a debris cavity extending axially therein, a cutting lid with cutting edges and debris passages, said cutting lid being detachably secured to said boss to close said debris cavity, whereby said shaft and said cutting lid can be rotatably driven as a unit and bone debris removed from the patella can be retained in said debris cavity.

2. The tool of claim 1 wherein said cutting edges are substantially parallel to said top of said cutting lid and are disposed to cut upon rotation of said shaft.

3. The tool of claim 1 wherein said cutting edges are spirally arranged.

4. The tool of claim 1 wherein said cutting edges upon rotation of said cutting lid about said axis each sweep an area overlapped by other of said cutting edges a total of about one and one-half times.

5. The tool of claim 1 wherein said cutting lid is disk shaped.

6. The tool of claim 1 wherein said cutting lid disposable.

7. The tool of claim 1 wherein said cutters extend from said top of said cutting lid angular to said axis a height of about 0.03 inches, said cutting edges being parallel to said cutting lid having length of about 0.25 inches whereby said tool resists blunting and cuttings can be collected in said bore.

8. The tool of claim 1 wherein said cutting edges are radial of said lid.

9. The tool of claim 1 wherein said cutting edges are on radii about 45° apart.

10. A patella cutter comprising a shaft having an axis of rotation and a tool end and a collet end, a boss on said tool end, a thumb trigger, said thumb trigger being slidable on said shaft between an extended position and a retracted position, a cutting lid with cutting edges and debris passages, a debris cavity extending axially into said boss, said shaft and said boss and said debris cavity being adjusted to be rotatably driven as a unit from said collet end, said cutting lid being detachably secured to said boss, a pair of oppositely disposed pins extending from said thumb trigger axially of said boss, said pins having upwardly extending throats secured to their ends, said throats having enlarged distal ends secured thereto, said boss having a pair of pin bores, said pins being in said pin bores, said enlarged distal ends and said pins and said pin bores having about equal radii, said throats having a smaller radius, said pin ends being flush with said debris cavity top and said throat and said enlarged distal ends upwardly extending from said top when said boss is in said extended position.

11. The patella cutter of claim 10 wherein a coil spring is circumferentially positioned about said shaft between said boss and thumb trigger, said coil spring biasing said thumb trigger into its retracted position.

12. The patella cutter of claim 10 wherein said cutting lid has a plurality of cutters with cutting edges extending therefrom, a pair of first bores extending through said cutting lid, pins being in said bores, said cutting edges being staggered to cover the entire area of said cutting lid, said cutting lid having debris passages therein whereby said cutting lid may be retained on said boss and securely fastened to said shaft and the debris collected in said debris cavity.

13. The patella cutter of claim 10 wherein said cutting lid has a top, said top having a pair of oppositely disposed first bores extending therethrough, said first bores having smaller portions extending therefrom, said smaller portions being larger than said throats and smaller than said enlarged distal ends, said smaller portions being deformed, whereby said smaller portions are congruous with the circular shape of said top and said cutting lid.

14. The patella cutter of claim 13 Wherein said pair of first bores have enlarged ends around their perimeter, said enlarged ends extending into said top a depth equal to the height of said enlarged distal ends, whereby said distal ends are flush with said top of said cutting lid when said boss is in said locking position.

15. The tool of claim 14 whereing said lock comprises said pins having enlarged distal ends and throat, said bores having an enlarged portion and a smaller portion, said enlarged portions being larger than said distal ends, said smaller portion being larger than said throat and smaller than said distal ends, whereby said distal ends may be passed through said enlarged portion and said lid rotated with respect to said boss positioning said throat in said smaller portions.

16. The tool of claim 10 wherein said cutting edges are substantially parallel to said top of said cutting lid and are disposed to cut upon rotation of said shaft.

17. The tool of claim 10 wherein said cutting edges are spirally arranged.

18. The tool of claim 10 wherein said cutting edges upon rotation of said cutting lid about said axis each sweep an area overlapped by other of said cutting edges a total of about one and one-half times.

19. The tool of claim 10 wherein said cutting lid is disk shaped.

20. The tool of claim 10 wherein said cutting lid is disposable.

21. The tool of claim 10 wherein said cutters extend from said top of said cutting lid angular to said axis a height of about 0.03 inches, said cutting edges being parallel to said cutting lid having length of about 0.25 inches whereby said tool resists blunting and cuttings can be collected in said bore.

* * * * *